United States Patent [19]

Bander

[11] Patent Number: 5,773,292
[45] Date of Patent: Jun. 30, 1998

[54] ANTIBODIES BINDING PORTIONS, AND PROBES RECOGNIZING AN ANTIGEN OF PROSTATE EPITHELIAL CELLS BUT NOT ANTIGENS CIRCULATING IN THE BLOOD

[75] Inventor: Neil H. Bander, Chappaqua, N.Y.

[73] Assignee: Cornell University, Ithaca, N.Y.

[21] Appl. No.: 463,500

[22] Filed: Jun. 5, 1995

[51] Int. Cl.[6] .................. C07K 16/28; A61K 39/395; C12N 5/12; G01N 33/53

[52] U.S. Cl. .................. 435/332; 435/7.21; 435/7.23; 424/138.1; 424/141.1; 424/152.1; 424/155.1; 530/387.5; 530/387.7; 530/388.2; 530/388.8; 530/389.1; 530/389.7; 530/391.1; 530/391.3; 530/391.7

[58] Field of Search .................. 530/387.1, 387.7, 530/388.1, 388.8, 389.1, 389.7, 391.3, 391.7; 436/501, 503, 504; 435/7.1–7.95, 70.21, 172.2, 240.27, 333, 7.21, 7.23; 424/138.1, 141.1, 155.1

[56] References Cited

U.S. PATENT DOCUMENTS

| Re. 33,405 | 10/1990 | Chu et al. . |
|---|---|---|
| 4,446,122 | 5/1984 | Chu et al. . |
| 4,675,287 | 6/1987 | Reisfeld et al. . |
| 4,840,915 | 6/1989 | Bogoch . |
| 4,863,851 | 9/1989 | McEwan et al. . |
| 4,902,615 | 2/1990 | Freeman et al. . |
| 4,970,299 | 11/1990 | Bazinet et al. . |
| 5,055,404 | 10/1991 | Ueda et al. . |
| 5,118,611 | 6/1992 | Smith et al. . |
| 5,130,129 | 7/1992 | Pardridge . |
| 5,135,737 | 8/1992 | Keana . |
| 5,242,824 | 9/1993 | Hellstrom et al. . |
| 5,250,297 | 10/1993 | Grauer et al. . |
| 5,367,060 | 11/1994 | Vandlen et al. . |

OTHER PUBLICATIONS

Webb, Cancer Immunol Immunother 17:7–17, 1984.
Raynor JNCI 73:617–623, 1984.
Raynor The Prostate 9:21–31, 1986.
Ware Cancer Research 42:1215–1222, 1982.
Carroll Clin. Immunol Immunopathol 33:268–281, 1984.
Lopes Cancer Research 50:6423–6429 1990.
Starling Cancer Research 46:367–374 1986.
Theyer J. Urology 150: 1544–1547, 1993.
Leroy, Cancer 64: 1–5 1989.
Seaver, Gen. Eng. News V14, pp. 10–21, Aug. 1994.
Colher, Methods in Enzymology 121: 802–816 1986.
Bayer, *Clinical Laboratory Methods*, 9th ed., St. Louis: C. V. Mosby Company, Chapter 35, "Clinical Serology," pp. 1025–1063 (1982).
Raynor et al., "Localization of a Normal Prostatic Secretory Product Using the Monoclonal Antibody, KR–P8," *Federation Proceedings*, 44:793 (1985).
Raynor et al., "Localization of a Normal Prostatic Secretory Product Using the Monoclonal Antibody, KR–P8," *Journal of Urology*, 134:384–387 (1985).
Guinan et al., "An Evaluation of Prostate Specific Antigen in Prostatic Cancer," *Journal of Urology*, 137:686–689 (1987).
Guinan et al., "Methods of Early Diagnosis in Genitourinary Cancer," *Cancer*, 60:668–676 (1987).
Harlow et al., *Antibodies: A Laboratory Manual*, Cold Spring Harbor, New York:Cold Spring Harbor Laboratory, Chapter 14, "Immunoassays," pp. 553–612 (1988).
Vitetta et al., "Redesigning Nature's Poisons top Create Anti–Tumor Reagents," *Science*, 238:1098–1104 (1987).
Dillman, "Monoclonal Antibodies for Treating Cancer," *Annals of Internal Medicine*, 111:592–602 (1989).
Waldmann, "Monoclonal Antibodies in Diagnosis and Therapy," *Science*, 252:1657–1662 (1991).

*Primary Examiner*—Lila Feisee
*Assistant Examiner*—Nancy A. Johnson
*Attorney, Agent, or Firm*—Nixon, Hargrave, Devans & Doyle

[57] ABSTRACT

The present invention is directed to the use of antibodies or binding portions thereof or probes which recognize an antigen of normal, benign, hyperplastic, and cancerous prostate epithelial cells or portions thereof. These antibodies or binding portions thereof or probes can be labeled and used for detection of such cells. They also can be used alone or bound to a substance effective to ablate or kill such cells as a therapy for prostate cancer. Also disclosed is a hybridoma cell line which produces a monoclonal antibody recognizing antigens of normal, benign, hyperplastic, and cancerous prostate epithelial cells or portions thereof.

19 Claims, 7 Drawing Sheets

ANTIBODIES BINDING PORTIONS, AND PROBES RECOGNIZING AN ANTIGEN OF PROSTATE EPITHELIAL CELLS BUT NOT ANTIGENS CIRCULATING IN THE BLOOD

FIELD OF THE INVENTION

The present invention relates to the treatment and diagnosis of prostate cancer with antibodies or binding portions thereof.

BACKGROUND OF THE INVENTION

Prostate cancer is the most common cancer in men with an estimated 244,000 cases in 1995 in the United States. It is the second leading cause of death among men who die from neoplasia with an estimated 44,000 deaths per year. Prompt detection and treatment is needed to limit mortality caused by prostate cancer.

Detection of Prostate Cancer

When it metastasizes, prostatic cancer has a distinct predilection for bone and lymph nodes. Saitoh, H., et al., "Metastatic Patterns of Prostatic Cancer. Correlation Between Sites And Number Of Organs Involved." *Cancer*, 54:3078–3084 (1984). At the time of clinical diagnosis, as many as 25% of patients have bone metastasis demonstrable by radionuclide scans. Murphy, G. P., et al., "The National Survey Of Prostate Cancer In The United States By The American College Of Surgeons," *J. Urol.*, 127:928–939 (1982). Accurate clinical evaluation of nodal involvement has proven to be difficult. Imaging techniques such as computed tomography ("CT") or magnetic resonance ("MR") imaging are unable to distinguish metastatic prostate cancer involvement of lymph nodes by criterion other than size (i.e., >1 cm). Therefore, by definition, these imaging modalities are inherently insensitive in the detection of small volume (<1 cm) disease as well as non-specific in the detection of larger volume adenopathy. A recent study assessed the accuracy of MR in patients with clinically localized prostate cancer. Rifkin, M. D., et al., "Comparison Of Magnetic Resonance Imaging And Ultrasonography In Staging Early Prostate Cancer," *N. Engl. J. Med.*, 323:621–626 (1990). In this study, 194 patients underwent an MR and 185 of these patients had a lymph node dissection. 23 (13w) patients had pathologically involved lymph nodes. MR was suspicious in only 1 of these 23 cases resulting in a sensitivity of 4%. Similar results have also been noted with CT scans. Gasser, T. C., et al., "MRI And Ultrasonography In Staging Prostate Cancer," *N. Engl. J. Med.* (Correspondence), 324(7):49–495 (1991).

The elevation of serum acid phosphatase activity in patients having metastasized prostate carcinoma was first reported by Gutman et al., *J. Clin. Invest* 17:473 (1938). In cancer of the prostate, prostatic acid phosphatase is released from the cancer tissue into the blood stream with the result that the total serum acid phosphatase level can be greatly increased above normal values. Numerous studies of this enzyme and its relation to prostatic cancer have been made since that time, e.g. Yam, *Amer. J. Med.* 56:604 (1974). However, the measurement of serum acid phosphatase is elevated in about 65–90 percent of patients having carcinoma of the prostate with bone metastasis; in about 30 percent of patients without roentgenological evidence of bone metastasis; and in about only 5–10 percent of patients lacking clinically demonstrable metastasis.

Prior art attempts to develop a specific test for prostatic acid phosphatase have met with only limited success, because techniques which rely on enzyme activity on a so-called "specific" substrate cannot take into account other biochemical and immunochemical differences among the many acid phosphatases which are unrelated to enzyme activity of prostate origin. In the case of isoenzymes, i.e. genetically defined enzymes having the same characteristic enzyme activity and a similar molecular structure but differing in amino acid sequences and/or content and, therefore, immunochemically distinguishable, it would appear inherently impossible to distinguish different isoenzyme forms merely by the choice of a particular substrate. It is, therefore, not surprising that none of these prior art methods is highly specific for the direct determination of prostatic acid phosphatase activity; e.g. see *Cancer* 5:236 (1952); *J. Lab. Clin. Med.* 82:486 (1973); *Clin. Chem. Acta.* 44:21 (1973); and *J. Physiol. Chem.* 356:1775 (1975).

In addition to the aforementioned problems of non-specificity which appear to be inherent in many of the prior art reagents employed for the detection of prostate acid phosphatase, there have been reports of elevated serum acid phosphatase associated with other diseases, which further complicates the problem of obtaining an accurate clinical diagnosis of prostatic cancer. For example, Tuchman et al., *Am. J. Med.* 27:959 (1959) noted that serum acid phosphatase levels appear to be elevated in patients with Gaucher's disease.

Due to the inherent difficulties in developing a "specific" substrate for prostrate acid phosphatase, several researchers have developed immunochemical methods for the detection of prostate acid phosphatase. However, the previously reported immunochemical methods have drawbacks of their own which have precluded their widespread acceptance. For example, Shulman et al., *Immunology* 93:474 (1964) described an immuno-diffusion test for the detection of human prostate acid phosphatase. Using antisera prepared from a prostatic fluid antigen obtained by rectal massage from patients with prostatic disease, no cross-reactivity precipitin line was observed in the double diffusion technique against extracts of normal kidney, testicle, liver, and lung. However, this method has the disadvantages of limited sensitivity, even with the large amounts of antigen employed, and of employing antisera which may cross-react with other, antigenically unrelated serum protein components present in prostatic fluid.

WO 79/00475 to Chu et. al. describes a new method for the detection of prostatic acid phosphatase isoenzyme patterns associated with prostatic cancer which obviates many of the above drawbacks. However, practical problems are posed by the need for a source of cancerous prostate tissue from which the diagnostically relevant prostatic acid phosphatase isoenzyme patterns associated with prostatic cancer are extracted for the preparation of antibodies thereto.

In recent years, considerable effort has been spent to identify enzyme or antigen markers for various types of malignancies with the view towards developing specific diagnostic reagents. The ideal tumor marker would exhibit, among other characteristics, tissue or cell-type specificity, and would be released into the circulation or other biological milieu which is easily obtained from individuals. Previous investigators have demonstrated the occurrence of human prostrate tissue-specific antigens.

Treatment of Prostate Cancer

As described in W. J. Catalona, "Management of Cancer of the Prostate," *New Engl. J. Med.* 331(15):996–1004 (1994), the management of prostate cancer can be achieved by watchful waiting, curative treatment, and palliation.

For men with a life expectancy of less than 10 years, watchful waiting is appropriate where low-grade, low-stage prostate cancer is discovered at the time of a partial prostatectomy for benign hyperplasia. Such cancers rarely progress during the first five years after detection. On the other hand, for younger men, curative treatment is often more appropriate.

Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. However, the use of prostate-specific antigen testing has permitted early detection of prostate cancer. As a result, surgery is less expensive with fewer complications. Patients with bulky, high-grade tumors are less likely to be successfully treated by radical prostatectomy.

After surgery, if there are detectable serum prostate-specific antigen concentrations, persistent cancer is indicated. In many cases, prostate-specific antigen concentrations can be reduced by radiation treatment. However, this concentration often increases again within two years.

Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, conformal radiation therapy where the field of radiation is designed to conform to the volume of tissue treated, and interstitial-radiation therapy where seeds of radioactive compounds are implanted using ultrasound guidance.

For treatment of patients with locally advanced disease, hormonal therapy before or following radical prostatectomy or radiation therapy has been utilized. Hormonal therapy is the main form of treating men with disseminated prostate cancer. Orchiectomy reduces serum testosterone concentrations, while estrogen treatment is similarly beneficial. Diethylstilbestrol from estrogen is another useful hormonal therapy which has a disadvantage of causing cardiovascular toxicity. When gonadotropin-releasing hormone agonists are administered testosterone concentrations are ultimately reduced. Flutamide is a nonsteroidal, antiandrogen agent that blocks binding of testosterone to its intracellular receptors. As a result, it blocks the effect of testosterone, increasing serum testosterone concentrations and allows patients to remain potent—a significant problem after radical prostatectomy and radiation treatments.

Cytotoxic chemotherapy is largely ineffective in treating prostate cancer. Its toxicity makes such therapy unsuitable for elderly patients. In addition, prostate cancer is relatively resistant to cytotoxic agents.

Use of Monoclonal Antibodies in Prostate Cancer Detection and Treatment

Theoretically, radiolabeled monoclonal antibodies ("mAbs") offer the potential to enhance both the sensitivity and specificity of detecting prostatic cancer within lymph nodes and elsewhere. While many mAbs have previously been prepared against prostate related antigens, none of these mAbs were specifically generated with an imaging objective in mind. Nevertheless, the clinical need has led to evaluation of some of these mAbs as possible imaging agents. Vihko, P., et al., "Radioimaging of Prostatic Carcinoma With Prostatic Acid Phosphatase—Specific Antibodies," *Biotechnology in Diagnostics,* 131–134 (1985); Babaian, R. J., et al., "Radioimmunological Imaging of Metastatic Prostatic Cancer With 111-Indium-Labeled Monoclonal Antibody PAY 276," *J. Urol.,* 137:439–443 (1987); Leroy, J M., et al., "Radioimmunodetection Of Lymph Node Invasion In Prostatic Cancer. The Use Of Iodine 123 (123-I)-Labeled Monoclonal Anti-Prostatic Acid Phosphatase (PAP) 227 A F (ab') 2 Antibody Fragments In Vivo," *Cancer,* 64:1–5 (1989); Meyers, J. F., et al., "Development Of Monoclonal Antibody Imaging Of Metastatic Prostatic Carcinoma," *The Prostate,* 14:209–220 (1989).

In some cases, the monoclonal antibodies developed for detection and/or treatment of prostate cancer recognize antigens specific to malignant prostatic tissues. Such antibodies are thus used to distinguish malignant prostatic tissue (for treatment or detection) from benign prostatic tissue. See U.S. Pat. No. 4,970,299 to Bazinet et al. and U.S. Pat. No. 4,902,615 to Freeman et al.

Other monoclonal antibodies react with surface antigens on all prostate epithelial cells whether cancerous or benign. See U.S. Pat. No. 4,446,122 and Re 33,405 to Chu et al., U.S. Pat. No. 4,863,851 to McEwan et al., and U.S. Pat. No. 5,055,404 to Ueda et al. However, the antigens detected by these monoclonal antibodies are present in the blood and, therefore, compete with antigens at tumor sites for the monoclonal antibodies. This causes background noise which makes the use of such antibodies inappropriate for in vivo imaging. In therapy, such antibodies, if bound to a cytotoxic agent, could be harmful to other organs.

The present invention is directed to overcoming the deficiencies of prior art antibodies in diagnosing and treating prostate cancer.

SUMMARY OF THE INVENTION

One aspect of the present invention relates to a method of ablating or killing normal, benign, hyperplastic, and cancerous prostate epithelial cells. The process involves providing an antibody or binding portion thereof or probe which recognizes an antigen (such as a surface antigen) of such cells but substantially no antigens circulating in the blood. The antibody or binding portion thereof or probe can be used alone or is bound to a substance effective to kill the cells upon binding of the antibody or binding portion thereof or probe to the cells. These antibodies or binding portions thereof or probes are then contacted with the cells under conditions effective to permit both binding of the antibody or binding portion thereof or probe to the antigens and killing or ablating of the cells.

Another aspect of the present invention relates to a method of detecting normal, benign, hyperplastic, and cancerous epithelial cells or portions thereof in a biological sample. This method involves providing an antibody or binding portion thereof or probe which recognizes an antigen of the cells but substantially no antigens circulating in the blood. The antibody or binding portion thereof or probe is bound to a label effective to permit detection of the cells or portions thereof upon binding of the antibody or binding portion thereof or probe to the cells or portions thereof. The biological sample is contacted with the antibody or binding portion thereof or probe having a label under conditions effective to permit binding of the antibody or binding portion thereof or probe to the antigen of any of the cells or portions thereof in the biological sample. The presence of any cells or portions thereof in the biological sample is detected by detection of the label.

Another aspect of the present invention pertains to an isolated antibody or binding portion thereof or probe recognizing an antigen of normal, benign, hyperplastic, and cancerous prostate epithelial cells or portions thereof but substantially no antigens circulating in the blood. A hybridoma cell line that produces monoclonal antibodies of this type and an antigen recognized by these monoclonal antibodies are also disclosed.

BRIEF DESCRIPTION OF THE DRAWINGS

In FIG. 4A, binding of Prost 130-biotin to antigens captured by Prost 130 was inhibited by Prost 130 but not by Prost 185. In FIG. 4B, binding of Prost 185-biotin to antigens captured by Prost 130 was inhibited by Prost 185 but not by Prost 130.

DETAILED DESCRIPTION OF THE INVENTION

Figure 1A:
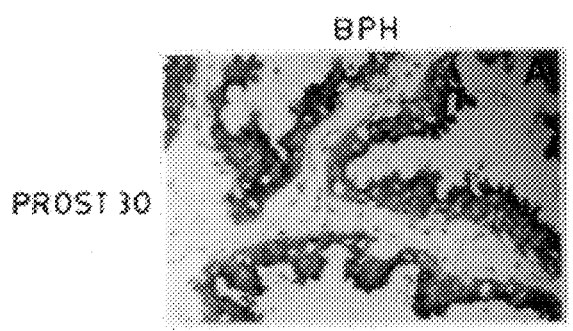
FIGS. 1A, 1B, 1C and 1D show immunohistochemical staining of benign prostate hyperplasia (FIGS. 1A and C) and prostate cancer (FIGS. 1B and D) with Prost 30 (FIGS. 1A and B) and Prost 410 (FIGS. 1C and D). Epithelial cells and luminal spaces were strongly stained. Prost 30 demonstrates enhanced immunoreactivity at the cell surface. Magnification×350 (FIGS. 1A, C and D), ×175 (FIG. 1B).
Figure 1B:
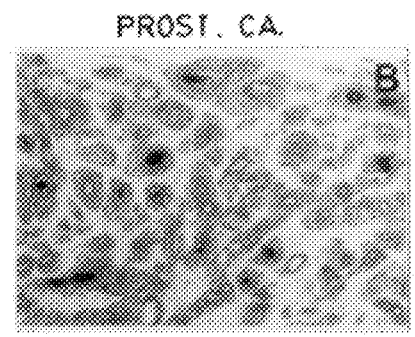
Figure 1C:
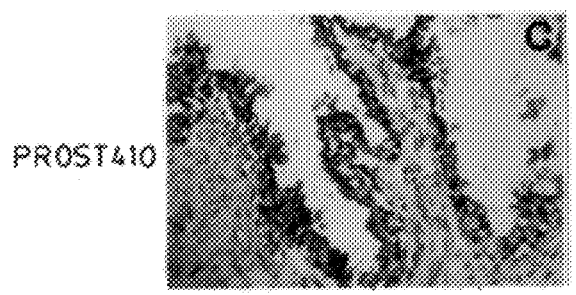
Figure 1D:
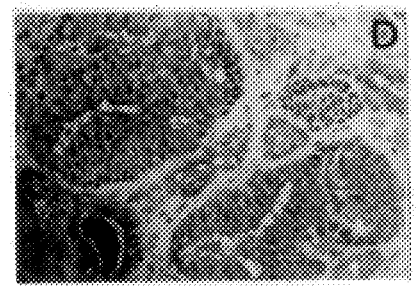

One aspect of the present invention relates to a method of ablating or killing normal, benign, hyperplastic, and cancerous prostate epithelial cells. The process involves providing an antibody or binding portion thereof or probe which recognizes an antigen (such as a surface antigen) of such cells but substantially no antigens circulating in the blood. The antibody or binding portion thereof or probe can be used alone or is bound to a substance effective to kill the cells upon binding of the antibody or binding portion thereof or probe to the cells. These antibodies or binding portions thereof or probes are then contacted with the cells under conditions effective to permit both binding of the antibody or binding portion thereof or probe to the antigens and killing or ablating of the cells. In its preferred form, such contacting is carried out in a living mammal by administering the antibody or binding portion thereof or probe to the mammal under conditions effective to permit both binding of the antibody or binding portion thereof or probe to the antigens and killing or ablating of the cells. Such administration can be carried out orally or parenterally.

Another aspect of the present invention relates to a method of detecting normal, benign, hyperplastic, and cancerous epithelial cells or portions thereof in a biological sample. This method involves providing an antibody or binding portion thereof or probe which recognizes an antigen of the cells but substantially no antigens circulating in the blood. The antibody or binding portion thereof or probe is bound to a label effective to permit detection of the cells or portions thereof upon binding of the antibody or binding portion thereof or probe to the cells or portions thereof. The biological sample is contacted with the antibody or binding portion thereof or probe having a label under conditions effective to permit binding of the antibody or binding portion thereof or probe to the antigen of any of the cells or portions thereof in the biological sample. The presence of any cells or portions thereof in the biological sample is detected by detection of the label. In its preferred form, such contacting is carried out in a living mammal and involves administering the antibody or binding portion thereof or probe to the mammal under conditions effective to permit binding of the antibody or binding portion thereof or probe to the antigen of any of the cells or portions thereof in the biological sample. Again, such administration can be carried out orally or parenterally. Alternatively, the contacting step can be carried out in a sample of serum or urine or other body fluids.

Antibodies suitable for either killing, ablating, or detecting normal, benign, hyperplastic, and cancerous prostate epithelial cells can be monoclonal or polyclonal. In addition, antibody fragments, half-antibodies, hybrid derivatives, and probes may be utilized. These antibodies, binding portions thereof, or probes recognize cell antigens or portions thereof in normal, benign, hyperplastic, and cancerous prostate epithelial cells. However, these antibodies, binding portions thereof, or probes bind to substantially no antigens in the blood. As a result, binding of the antibodies or binding portions thereof or probes is concentrated in areas where there are large numbers of prostate epithelial cells or portions thereof.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in E. Harlow, et. al., editors, *Antibodies: A Laboratory Manual* (1988), which is hereby incorporated by reference.

In addition to utilizing whole antibodies, the processes of the present invention encompass use of binding portions of such antibodies. Such binding portions include Fab fragments, F(ab')$_2$ fragments, and Fv fragments. These antibody fragments can be made by conventional procedures, such as proteolytic fragmentation procedures, as described in J. Goding, *Monoclonal Antibodies: Principles and Practice*, pp. 98–118 (N.Y. Academic Press 1983), which is hereby incorporated by reference.

Alternatively, the processes of the present invention can utilize probes found either in nature or prepared synthetically by recombinant DNA procedures or other biological procedures. Suitable probes are molecules which bind to prostate-related antigens identified by the monoclonal antibodies of the present invention. Such probes can be e.g., proteins, peptides, lectins, or nucleic acid probes.

Here, it is preferred to utilize the monoclonal antibodies identified below in Table 1:

TABLE 1

| Monoclonal Antibody Name | ATCC Designation for Hybridoma Cell Line |
| --- | --- |
| Prost 30 | HB 11424 |
| Prost 185 | HB 11425 |
| Prost 410 | HB 11426 |
| Prost 130 | HB 11427 |
| C37 | HB 11892 |
| C219 | HB 11893 |

It is particularly desirable to utilize a mixture of these antibodies or other antibodies to treat or image prostate epithelial cells with varying surface antigen characteristics.

The present invention also relates to antigens of normal, benign, hyperplastic, and cancerous prostate epithelial cells recognized by the monoclonal antibodies in Table 1.

Regardless of whether the antibodies or binding portions thereof or probes are used for treatment or therapy, they can be administered orally, parenterally, subcutaneously, intravenously, intramuscularly, intraperitoneally, by intranasal instillation, by intracavitory or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the antibody or binding portion thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The antibody or binding portion thereof or probes of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the antibody or binding portion thereof or probe of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The antibodies or binding portions thereof or probes may be utilized to detect normal, benign, hyperplastic, and cancerous prostate epithelial cells in vivo. This is achieved by labeling the antibody or binding portion thereof or probe administering the labeled antibody or binding portion thereof or probe to a mammal, and then imaging the mammal.

Examples of labels useful for diagnostic imaging in accordance with the present invention are radiolabels such as $^{131}$I, $^{111}$In, $^{123}$I, $^{99}$mTc, $^{32}$P, $^{125}$I, $^{3}$H, $^{14}$C, and $^{188}$Rh, fluorescent labels such as fluorescein and rhodamine, nuclear magnetic resonance active labels, chemiluminescers such as luciferin, and enzymatic markers such as peroxidase or phosphatase. The antibody or binding portion thereof or probe can be labeled with such reagents using techniques known in the art. For example, see Wensel and Meares, *Radioimmunoimaging and Radioimmunotherapy*, Elsevier, N.Y. (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", *Meth. Enzymol.* 121: 802–816 (1986), which is hereby incorporated by reference.

A radiolabeled antibody or binding portion thereof or probe of this invention can be used for in vitro diagnostic tests. The specific activity of a tagged antibody, binding portion thereof, or probe depends upon the half-life, the isotopic purity of the radioactive label, and how the label is incorporated into the antibody or binding portion thereof or probe. Table 2 lists several commonly-used isotopes, their specific activities and half-lives. In immunoassay tests, the higher the specific activity, in general, the better the sensitivity.

TABLE 2

| Isotope | Specific Activity of Pure Isotope (Curies/mole) | Half-Life |
| --- | --- | --- |
| $^{14}C$ | $6.25 \times 10^{1}$ | 5720 years |
| $^{3}H$ | $2.01 \times 10^{4}$ | 12.5 years |
| $^{35}S$ | $1.50 \times 10^{6}$ | 87 days |
| $^{125}I$ | $2.18 \times 10^{6}$ | 60 days |
| $^{32}P$ | $3.16 \times 10^{6}$ | 14.3 days |
| $^{131}I$ | $1.62 \times 10^{7}$ | 8.1 days |

Procedures for labeling antibodies, binding portions thereof, or probes with the radioactive isotopes listed in Table 2 are generally known in the art. Tritium labeling procedures are described in U.S. Pat. No. 4,302,438, which is hereby incorporated by reference. Iodinating, tritium labeling, and $^{35}S$ labeling procedures especially adapted for murine monoclonal antibodies are described by Goding, J. W. (supra, pp 124–126) and the references cited therein, which are hereby incorporated by reference. Other procedures for iodinating antibodies, binding portions thereof, or probes are described by Hunter and Greenwood, *Nature* 144:945 (1962), David et al., *Biochemistry* 13:1014–1021 (1974), and U.S. Pat. Nos. 3,867,517 and 4,376,110, which are hereby incorporated by reference. Radiolabeling elements which are useful in imaging include $^{123}I$, $^{131}I$, $^{111}In$, and $^{99m}TC$ for example. Procedures for iodinating antibodies, binding portions thereof, or probes are described by Greenwood, F. et al., *Biochem. J.* 89:114–123 (1963); Marchalonis, J., *Biochem. J.* 113:299–305 (1969); and Morrison, M. et al., *Immunochemistry,* 289–297 (1971), which are hereby incorporated by reference. Procedures for $^{99m}Tc$-labeling are described by Rhodes, B. et al. in Burchiel, S. et al. (eds.), *Tumor Imaging: The Radioimmunochemical Detection of Cancer,* New York: Masson 111–123 (1982) and the references cited therein, which are hereby incorporated by reference. Procedures suitable for $^{111}In$-labeling antibodies, binding portions thereof, or probes are described by Hnatowich, D. J. et al., *J. Immul. Methods,* 65:147–157 (1983), Hnatowich, D. et al., *J. Applied Radiation,* 35:554–557 (1984), and Buckley, R. G. et al., *F. E. B. S.* 166:202–204 (1984), which are hereby incorporated by reference.

In the case of a radiolabeled antibody, binding portion thereof, or probe, the antibody, binding portion thereof, or probe is administered to the patient, is localized to the tumor bearing the antigen with which the antibody, binding portion thereof, or probe reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy,* R. W. Baldwin et al., (eds.), pp. 65–85 (Academic Press 1985), which is hereby incorporated by reference. Alternatively, a positron emission transaxial tomography scanner such as designated Pet VI located at Brookhaven National Laboratory can be used where the radiolabel emits positrons (e.g., $^{11}C$, $^{18}F$, $^{15}O$ and $^{13}N$).

Fluorophore and chromophore labeled antibodies, binding portions thereof, or probes can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science,* 162:526 (1968) and Brand, L. et al., *Annual Review of Biochemistry,* 41:843–868 (1972), which are hereby incorporated by reference. The antibodies, binding portions thereof, or probes can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above are the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies or binding portions thereof or probes can be labeled with fluorchromes or chromophores by the procedures described by Goding, J. (supra, pp 208–249). The antibodies or binding portions thereof or probes can be labeled with an indicating group containing the NMR-active $^{19}F$ atom, or a plurality of such atoms inasmuch as (i) substantially all of naturally abundant fluorine atoms are the $^{19}F$ isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body NMR determination is carried out using an apparatus such as one of those described by Pykett, *Scientific American,* 246:78–88 (1982), which is hereby incorporated by reference, to locate and image prostate epithelial cells.

The antibodies or binding portions thereof or probes can also be utilized to kill or ablate normal, benign, hyperplastic, and cancerous prostate epithelial cells in vivo. This involves using the antibodies or binding portions thereof or probes by themselves or with a cytotoxic drug, which the antibodies, binding portions thereof, or probes to normal, benign, hyperplastic, and cancerous prostate epithelial cells where those cells are ablated or killed. This involves administering the antibodies or binding portions thereof or probes bonded to a cytotoxic drug to a mammal requiring such treatment. Since the antibodies or binding portions thereof or probes recognize prostate epithelial cells, any such cells to which the antibodies or binding portions thereof or probes bind are destroyed. Although such administration may destroy normal prostate epithelial cells, this is not problematic, because the prostate is not required for life or survival. Although the prostate may indirectly contribute to fertility, this is not likely to be a practical consideration in patients receiving the treatment of the present invention.

The antibodies or binding portions thereof or probes of the present invention may be used to deliver a variety of cytotoxic drugs including therapeutic drugs, a compound emitting radiation, molecules of plants, fungal, or bacterial origin, biological proteins, and mixtures thereof.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, *gelonin, mitogillin, restrictocin, phenomycin,* and *enomycin,* for example. Procedures for preparing enzymatically active polypeptides of the immunotoxins are described in W084/03508 and W085/03508, which are hereby incorporated by reference. Certain cytotoxic moieties are derived from adriamycin, chlorambucil, daunomycin, methotrexate, neocarzinostatin, and platinum, for example.

Procedures for conjugating the antibodies or binding portions thereof or probes with the cytotoxic agents have been previously described. Procedures for conjugating chlorambucil with antibodies are described by Flechner, I,. *European Journal of Cancer,* 9:741–745 (1973); Ghose, T. et al., *British Medical Journal,* 3:495–499 (1972); and Szekerke, M., et al., *Neoplasma,* 19:211–215 (1972), which are hereby incorporated by reference. Procedures for conjugating daunomycin and adriamycin to antibodies are described by Hurwitz, E. et al., *Cancer Research,* 35:1175–1181 (1975) and Arnon, R. et al. *Cancer Surveys,* 1:429–449 (1982), which are hereby incorporated by reference. Procedures for preparing antibody-ricin conjugates are described in U.S. Pat. No. 4,414,148 and by Osawa, T., et al. *Cancer Surveys,* 1:373–388 (1982) and the references cited therein, which are hereby incorporated by reference. Coupling procedures as also described in EP 86309516.2, which is hereby incorporated by reference.

Alternatively, the antibody, binding portion thereof, or probe can be coupled to high energy radiation, e.g., a radioisotope such as 1311, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy,* R. W. Baldwin et al. (eds.), pp 303–316 (Academic Press 1985), which is hereby incorporated by reference. Radiotherapy is expected to be particularly effective, because prostate cancer is a relatively radiosensitive tumor.

The antibody or binding portion thereof or probe of the present invention can be used and sold together with equipment, as a kit, to detect the particular label.

The therapeutic use of the antibodies, binding portions thereof, or probes of the present invention can be used in conjunction with other therapeutic treatment modalities. Such other treatments include surgery, radiation, cryosurgery, thermotherapy, hormone treatment, chemotherapy, vaccines, and other immunotherapies.

Also encompassed by the present invention is a method of killing or ablating which involves using the antibodies, binding portions thereof, or probes for prophylaxis. For example, these materials can be used to prevent or delay development or progression of prostate cancer.

Use of the prostate cancer therapy of the present invention has a number of benefits. Since the antibodies or binding portions thereof or probes according to the present invention only target prostate epithelial cells, other tissue is spared. As a result, treatment with such antibodies or binding portions thereof or probes is safer, particularly for elderly patients. Treatment according to the present invention is expected to be particularly effective, because it directs high levels of antibodies or binding portions thereof or probes to the bone marrow and lymph nodes where prostate cancer metastases predominate. Moreover, tumor sites for prostate cancer tend to be small in size and, therefore, easily destroyed by cytotoxic agents. Treatment in accordance with the present invention can be effectively monitored with clinical parameters such as serum prostate specific antigen and/or pathological features of a patient's cancer, including stage, Gleason score, extracapsular, seminal, vesicle or perineural invasion, positive margins, involved lymph nodes, etc.

EXAMPLES

Example 1

Human Tissues.

Fresh specimens of benign and malignant tissues were provided by the Tumor Procurement Service of the Department of Pathology at the Memorial Sloan-Kettering Cancer Center.

A soluble tissue preparation ("SPTP") was prepared by initial mechanical mincing of fresh benign and malignant prostates. The tissue was homogenized for 1 min in a blade homogenizer in phosphate buffered saline ("PBS"), pH 7.2, containing 0.2 mM phenylmethylsulfonyl fluoride (Sigma Chemical, St. Louis, Mo.) and 20 u/ml aprotinin (Calbiochem, San Diego, Calif.). The homogenate was centrifuged at 100,000 g for 60 min at 4° C., and the supernatant was decanted and saved.

Example 2

Tissue Culture.

Cultured cell lines of human cancers were from the laboratory of Human Tumor Immunology, Memorial Sloan-Kettering Cancer Center. The prostate cancer cell lines PC-3 (Mickey, D. D., et al., "Characterization Of A Human Prostate Adenocarcinoma Cell Line (DU145) As A Monolayer Culture And As A Solid Tumor In Athymic Mice," *Prog. Clin. Biol. Res.,* 37:67–84 (1980), which is hereby incorporated by reference), DU-145 (Mickey, D. D., et al., "Characterization Of A Human Prostate Adenocarcinoma Cell Line (DU145) As A Monolayer Culture And As A Solid Tumor In Athymic Mice," *Prog. Clin. Biol. Res.,* 37:67–84 (1980), which is hereby incorporated by reference), and LNCaP (Horoszewicz, J. S., et al., "LNCaP Model Of Human Prostatic Carcinoma," *Cancer Res.,* 43:1809–1818 (1983), which is hereby incorporated by reference) were obtained from the American Type Culture Collection (Rockville, Md.). Hybridomas were initially cloned in RPMI-1640 medium supplemented with 10% FCS, 0.1 mM nonessential amino acids, 2 mM L-glutamine, 100 units/ml of penicillin, 100 ug/ml of streptomycin and HAT medium (GIBCO, Grand Island, N.Y.). Subclones were cultured in the same medium without aminopterin.

Example 3

Preparation of Mouse Monoclonal Antibodies

A BALB/c mouse was immunized subcutaneously with mechanically minced tissues from fresh benign hyperplastic and malignant prostate tissues three times at 1 week intervals. One week later, a final intraperitoneal immunization was administered. Three days later spleen cells were fused with SP-2 mouse myeloma cells utilizing standard techniques. Ueda, R., et al., "Cell Surface Antigens Of Human Renal Cancer Defined By Mouse Monoclonal Antibodies: Identification Of Tissue-Specific Kidney Glycoproteins," *Proc. Natl. Acad. Sci. USA,* 78:5122–5126 (1981), which is hereby incorporated by reference. Supernatants of the resulting clones were screened by immunohistochemistry. Clones which were reactive with benign prostate tissues, but not with normal lymph node, were selected and subcloned 3 times by limiting dilution. The immunoglobulin class of cultured supernatant from each clone was determined by immunodiffusion using specified rabbit antisera (Calbiochem, San Diego, Calif.). mAbs were purified using the MAPS-II kit (Bio-Rad, Richmond, Calif.).

Example 4
Biotinylation of mAbs

Purified mAbs were dialyzed in 0.1M NaCo$_3$ for 2 hours. One ml of mAb at 1 mg/ml was mixed with 0.1 ml of biotinamidocaproate N-hydroxysuccinamide ester (Sigma) 1 mg/ml in dimethylsulfoxide and stirred for 4 hours at room temperature. Unbound biotin was removed by dialysis against PBS.

Example 5
Immunohistochemical Staining.

For the initial screening of hybridomas, cryostat sections of prostate tissues were placed inside rings of Falcon 3034 plate covers (Becton-Dickenson, Lincoln Park, N.J.) previously coated with 0.45% gelatin solution. Marusich, M. F., "A Rapid Method For Processing Very Large Numbers Of Tissue Sections For Immunohistochemical Hybridoma Screening," J. Immunol. Methods, 111:143–145 (1988), which is hereby incorporated by reference. Plates were stored at −80° C. Cryostat sections were fixed with 2% paraformaldehyde in PBS for 10 min at room temperature and, after washing with PBS, endogenous peroxidase activity was blocked by treatment with 0.3% hydrogen peroxide in PBS for 10 min at room temperature. After sections were incubated with 2% BSA in PBS for 20 min, mAbs were added for 60 min at room temperature. Slides were extensively washed with PBS and incubated with peroxidase-conjugated rabbit anti-mouse Ig (DAKO Corp., Santa Barbara, Calif.) diluted 1:100 in 10% normal human serum in PBS for 60 min at room temperature. After a diaminobenzidine reaction, sections were counterstained with hematoxylin.

To confirm cell surface expression of the detected antigens, fresh prostate tissue was mechanically dispersed into a single cell suspension by scraping the tissue sample and passing it through a 50 micron sieve. The cell suspension was washed, incubated with mAb for 1 hour at room temperature and then a rabbit anti-mouse Ig-fluorescein (DAKO Corp., Santa Barbara, Calif.). Slides were read with a fluorescent microscope. Negative control consisted of an isotype-matched irrelevant mAb, while an anti-class I MHC mAb served as a positive control.

Example 6
Serological Analysis

The anti-mouse immunoglobulin mixed hemadsorption assay was performed as previously described. Ueda, R., et al., "Cell Surface Antigens Of Human Renal Cancer Defined By Mouse Monoclonal Antibodies: Identification Of Tissue-Specific Kidney Glycoproteins," Proc. Natl. Acad. Sci. USA, 78:5122–5126 (1981), which is hereby incorporated by reference. To prepare the indicator cells, anti-mouse Ig (DAKO Corp.) was conjugated to type 0 human RBC using 0.01% chromium chloride. Serological assays were performed on cells previously plated in Terasaki plates (Nunc, Denmark). Antibodies were incubated with target cells at room temperature for 1 hour. Target cells were then washed and indicator cells added for 1 hour.

Example 7
mAb reactivity to prostatic acid phosphatase ("PAP")

Monoclonal antibody reactivity to prostatic acid phosphatase was assayed by direct ELISA. Serial dilutions of purified PAP (Calbiochem, La Jolla, Calif.) were adsorbed onto Terasaki plates overnight at 37° C. The plates were washed with PBS 0.5% BSA. PBS 2% BSA was incubated for 60 min at 37° C. to block non-specific binding. Biotinylated mAb was incubated for 45 min at room temperature. Rabbit anti-PAP (Sigma, St. Louis, Mo.) diluted 1/6000 in PBS 2% BSA served as positive control. Rabbit anti-PAP was followed by biotin-conjugated goat anti-rabbit Ig (Sigma) 1/5000 in PBS 2% BSA. Avidin-conjugated alkaline phosphatase Sigma 1/500 in PBS 2% BSA for 45 min at room temperature followed biotinylated antibody. A substrate of alkaline phosphatase (para nitrophenylphosphate) was incubated at 37° C., and reactivity was read at OD$_{405}$ nm on an Artek ELISA reader adapted for Terasaki plates. Negative controls omitted PAP antigen and/or Rabbit anti-PAP.

Example 8—mAb reactivity to prostate specific antigen ("PSA").

Monoclonal antibody reactivity to prostate specific antigen was assayed by a double antibody sandwich ELISA. Terasaki plates were coated with rabbit anti-PSA (Accurate Chemical and Scientific Corp, N.Y.) diluted 1/1000 in carbonate coating buffer overnight at 37° C. PBS 2% BSA was used to block non-specific binding. The soluble prostate tissue preparation ("SPTP") provided a source of PSA. SPTP was serially diluted in PBS 2% BSA and incubated at RT for 45 min. Biotinylated mAbs were added for 45 min. Avidin-conjugated alkaline phosphatase and substrate were used as described above for the direct ELISA. Negative controls omitted the Rabbit anti-PSA capture antiserum or the PSA (SPTP).

Example 9
Immunoprecipatation

SPTP was applied to a Concanavalin A column and eluted by 0.2M a-methyl D-mannoside. Fractions containing PSA were determined by a sandwich ELISA using Rabbit anti-PSA and biotin-conjugated Prost 410. Pooled PSA fractions were labelled with I-125 by the chloramide-T method. Unbound I-125 was removed with a PD10 column (BIO-RAD, Richmond, Calif.). Labelled antigen was precleared by normal mouse or rabbit sera once and precipitated with mAbs or polyclonal antibodies and protein A sepharose (Boehringer Manheim Biochem.) For sequential immunoprecipitations, labelled antigens were precleared with normal serum, precleared 3 times by first antibodies. Resulting supernatants were precipitated with second antibodies and protein A sepharose. Each precipitate was applied to 9% SDS-PAGE by the method of Laemmli. Laemmli, U.K., "Cleavage Of Structural Proteins During The Assembly Of The Head Of Bacteriophage T4," Nature (London), 227:680–685 (1970), which is hereby incorporated by reference.

Approximately 800 clones resulted from this fusion, of which six clones were initially selected based on immunohistochemical reactivity with prostate epithelium and the absence of reactivity with lymph node tissue. After subcloning, supernatants from the 6 hybridomas were assayed on a panel of cell lines using a mixed hemadsorption assay (Table 3).

TABLE 3

Reactivity of mAbs with human cell lines by rabbit anti-mouse Ig rosetting assay

| Cell lines | Prost 16 ($\gamma^1$) | Prost 30 ($\gamma^1$) | Prost 130 ($\gamma^1$) | Prost 185 ($\gamma^1$) | Prost 284 ($\mu$) | Prost 410 ($\gamma^1$) |
|---|---|---|---|---|---|---|
| Renal | | | | | | |
| SK-RC-18, 39, 4, 53, 42, | ●●○●● | ○○○○○ | ○○○○○ | ○○○○○ | ●●○●● | ○○○○○ |
| 8, 26, 31, 45, 48 | ○○○○○ | ○○○○○ | ○○○○○ | ○○○○○ | ○○○○○ | ○○○○○ |
| 1, 59, 21, 2, 44, | ○●●○ | ○○○○ | ○○○○ | ○○○○ | ○●●○ | ○○ |
| 47, 62, 28, 9, 17 | | | | | | |
| Caki-1 | ○ | ○ | ○ | ○ | ○ | ○ |
| Bladder | | | | | | |
| VmCUB-1, -2, 647V, RT4 | ●○●● | ○○○○ | ○○○○ | ○○○○ | ●○●● | ○○○○ |
| 253J, 5637, 639V, T234 | ○●○● | ○○○○ | ○○○○ | ○○○○ | ○●○● | ○○○○ |
| Prostate | ●●○ | ○○○ | ○○○ | ○○○ | ●●○ | ○○● |
| PC-3, Du145, LNCaP | | | | | | |
| Melanoma | | | | | | |
| SK-MEL-23, 28, 31, 37 | ○○○○ | ○○○○ | ○○○○ | ○○○○ | ○○○○ | ○○○○ |
| 173, 179 | ○○ | ○○ | ○○ | ○○ | ○○ | ○○ |
| Astrocytoma | | | | | | |
| SK-MG-1, 4, 5, 7 | ○○○○ | ○○○○ | ○○○○ | ○○○○ | ○○○○ | ○○○○ |
| 15, 17, 21, 22 | ○○○○ | ○○○○ | ○○○○ | ○○○○ | ○○○○ | ○○○○ |
| Colon | | | | | | |
| Sw1116, Sw480, HCT15, | ○●●● | ○○○○ | ○○○○ | ○○○○ | ○●●● | ○○○○ |
| HT29 | | | | | | |
| LS174T, SK-CO-11, | ○○● | ○○○ | ○○○ | ○○○ | ○○○ | ○○○ |
| SK-CO-17 | | | | | | |
| Lung | ○ | ○ | ○ | ○ | ○ | ○ |
| HCIH69 | | | | | | |
| Hematopoietic | | | | | | |
| SK-Ly-18, -16, DAUDI | ○○○ | ○○○ | ○○○ | ○○○ | ○○○ | ○○○ |
| BALL-1, HL-60, SK-DHL-2 | ○○○ | ○○○ | ○○○ | ○○○ | ○○○ | ○○○ |
| U937, RAMOS, RAJI | ○○○ | ○○○ | ○○○ | ○○○ | ○○○ | ○○○ |
| HSB2 | ○ | ○ | ○ | ○ | ○ | ○ |
| Pancreas | ● | ○ | ○ | ○ | ● | ○ |
| ASPC-1 | | | | | | |

Prost 16 and Prost 284 showed virtually identical reactivities; as Prost 284 was an IgM, it was put aside in favor of Prost 16, an IgG$_1$. Prost 410 reacted only with LNCaP, and Prost 30, Prost 130, and Prost 185 failed to react with any cell lines including the prostate cancer cell lines PC-3, DU 145, and LNCaP. After purification of the 5 selected mAbs using protein A columns, reactivities of these mAbs on normal human tissues were examined immunohistochemically (Table 4).

TABLE 4

Reactivity of mAbs with human normal tissues by indirect immunoperosidase staining

| Tissues | Prost 16 ($\gamma^1$) | Prost 30 ($\gamma^1$) | Prost 130 ($\gamma^{2a}$) | Prost 185 ($\gamma^1$) | Prost 410 ($\gamma^1$) |
|---|---|---|---|---|---|
| Prostate | ● | ● | ● | ● | ● |
| Kidney | | | | | |
| Glomerulus | ○ | ○ | ○ | ○ | ○ |
| Tubule | ● | ■ | ■ | ■ | ○ |
| Ureter | ● | ○ | ○ | ○ | ○ |
| Bladder | ● | ○ | ○ | ○ | ○ |
| Testis | ● | ○ | ○ | ○ | ○ |
| Uterus | | | | | |
| Cervix | ● | ○ | ○ | ○ | ○ |
| Endometrium | ● | ○ | ○ | ○ | ○ |
| Fallopian tube | ● | ○ | ○ | ○ | ○ |
| Placenta | ● | ○ | ● | ● | ○ |
| Umbilical cord | ○ | ○ | ○ | ○ | ○ |
| Cerebrum | ○ | ○ | ○ | ○ | ○ |
| Cerebellum | ○ | ○ | ○ | ○ | ○ |
| Thymus | ● | ○ | ● | ● | ○ |
| Parotid gland | ● | ○ | ● | ● | ○ |
| Breast | ● | ○ | ○ | ○ | ○ |
| Lung | | | | | |
| Alveola | ○ | ○ | ○ | ○ | ○ |
| Bronchiole | ● | ○ | ○ | ○ | ○ |
| Stomach | ● | ○ | ○ | ○ | ○ |
| Colon | ● | ○ | ● | ● | ○ |
| Pancreas | ● | ○ | ○ | ○ | ○ |
| Liver | ○ | ○ | ○ | ○ | ○ |
| Adrenal gland | ○ | ○ | ○ | ○ | ○ |
| Lymph node | ○ | ○ | ○ | ○ | ○ |
| Skin | ● | ○ | ○ | ○ | ○ |
| Foreskin | ● | ○ | ● | ○ | ○ |

● — positive; ■ — weak, heterogeneous; ○ — negative

Prost 16 showed broad reactivity and was not further characterized. Prost 130 and Prost 185 showed relatively restricted and almost identical reactivities. Prost 30 and Prost 410 showed highly restricted reactivities. None of these 5 mAbs demonstrated immunohistochemical reactivity with normal rat prostate nor the Dunning R-3327 rat prostate cancer cell line.

mAb Prost 30: Purified Prost 30 (40 ug/ml) did not react, by MHA, with any of an expanded panel of 74 human cell lines. By indirect immunoperoxidase assays, Prost 30 also failed to react with any of 29 cell lines (including LNCaP, PC-3, and DU 145) after 20 paraformaldehyde fixation. Immunohistochemical study of frozen tissue sections revealed all 35 benign and 30 malignant prostates were Prost 30-positive (FIG. 1). Prost 30 reacted with the prostatic epithelial cells and luminal secretions. No other tissues tested were reactive except for weak and heterogeneous reactivity with some tubules in 7 of 19 normal kidney specimens and 1 of 7 lung cancers (Tables 5 and 6).

TABLE 5

Immunohistochemical reactivity of mAbs with human normal tissues

| | Reactivity | | |
|---|---|---|---|
| | Prost 30 | Prost 130 | Prost 185 |
| Prostate | 35/35[a] | 35/35 | 35/35 |
| Kidney | 7/19 | 3/10 | 3/10 |
| Lung | 0/6 | 0/4 | 0/4 |
| Liver | 0/6 | 0/6 | 0/5 |
| Spleen | 0/4 | 0/3 | 0/3 |
| Thymus | 0/1 | 1/1 | 1/1 |
| Ureter | 0/9 | 0/5 | 0/5 |
| Bladder | 0/10 | 0/8 | 0/8 |
| Testis | 0/3 | 0/3 | 0/3 |
| Breast | 0/7 | 2/5 | 2/5 |
| Esophagus | 0/1 | 1/1 | 1/1 |
| Stomach | 0/3 | 2/2 | 1/2 |
| Small intestine | 0/2 | 1/2 | 1/2 |
| Colon | 0/4 | 3/4 | 2/4 |
| Pancreas | 0/1 | 0/1 | 0/1 |
| Uterus | 0/4 | 0/2 | 0/2 |
| Thyroid | 0/2 | 1/1 | 1/1 |
| Adrenal | 0/3 | 0/2 | 0/2 |
| Parotid | 0/2 | 2/2 | 2/2 |
| Submandibular gland | 0/1 | 1/1 | 1/1 |
| Skin | 0/2 | 0/2 | 0/2 |
| Cerebrum | 0/1 | 0/1 | 0/1 |
| Cerebellum | 0/1 | 0/1 | 0/1 |

[a]Number of specimens with positive staining/number of specimens tested. Based on relative endpoint titrations with all 3 mAbs, immunoreactivity on prostate tissue was 200–500 fold that on other positive tissues.

TABLE 6

Immunohistochemical reactivity of mAbs with human cancers

| | Reactivity | | |
|---|---|---|---|
| Cancer | Prost 30 | Prost 130 | Prost 185 |
| Prostate | 30/30[a] | 30/30 | 30/30 |
| Renal | 0/17 | 0/7 | 0/7 |
| Bladder | 0/21 | 0/8 | 0/8 |
| Lung | 1/7 | 1/4 | 1/4 |
| Breast | 0/6 | 2/6 | 2/6 |
| Colon | 0/5 | 3/6 | 2/6 |
| Ovary | 0/6 | 2/6 | 0/6 |
| Testis | 0/2 | n.t. | n.t. |

Figure 2A:
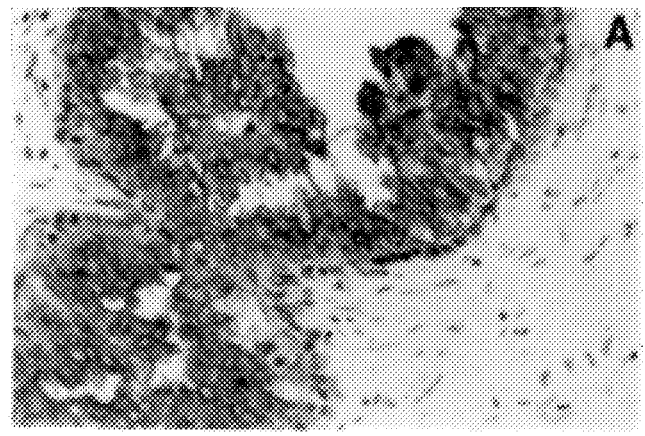
FIGS. 2A and 2B show immunohistochemical staining of BPH (i.e. prostatic epithelium) sections by mAb Prost 130 (FIG. 2A) and Prost 185 (FIG. 2B) at 5 ug/ml. Magnification×350.
Figure 2B:
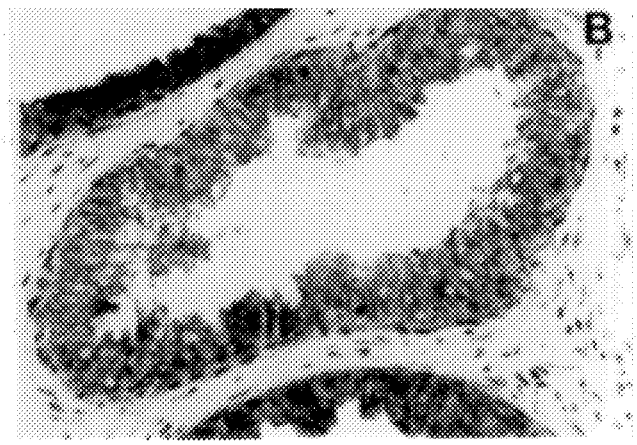
Figure 3A:
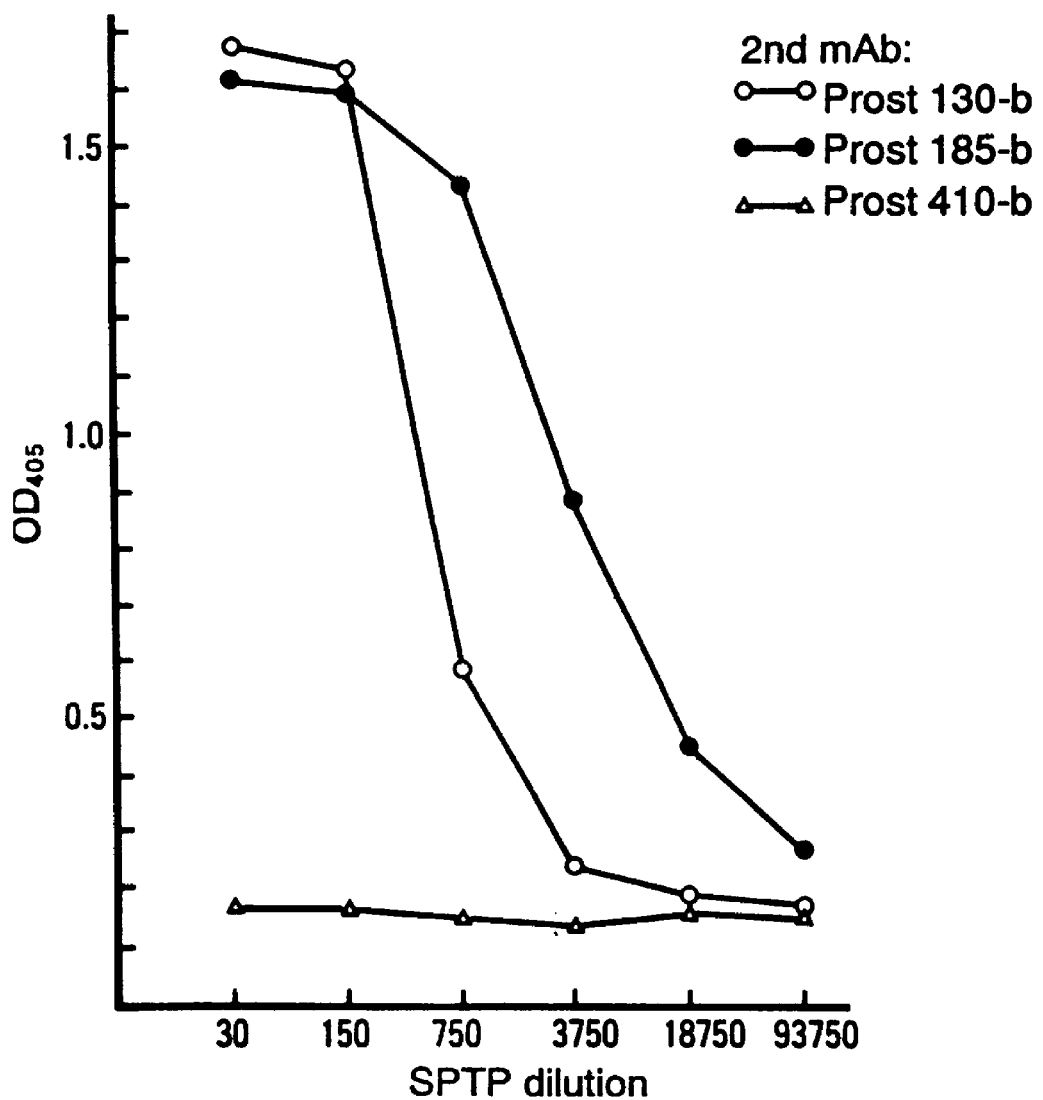
FIGS. 3A and 3B shows a sandwich ELISA in which Prost 130 (FIG. 3A) or Prost 185 (FIG. 3B) were coated on Terasaki plates with coating buffer overnight at 37° C. After adding solubilized prostate antigens, biotin conjugated mAbs were added. Prost 130-biotin and Prost 185-biotin reacted with antigens captured by Prost 130 (FIG. 3A). Prost 130 was inhibited by Prost 130 (FIG. 3A). Prost 130-biotin reacted with antigens captured by Prost 185, but Prost 185-biotin did not.
Figure 3B:
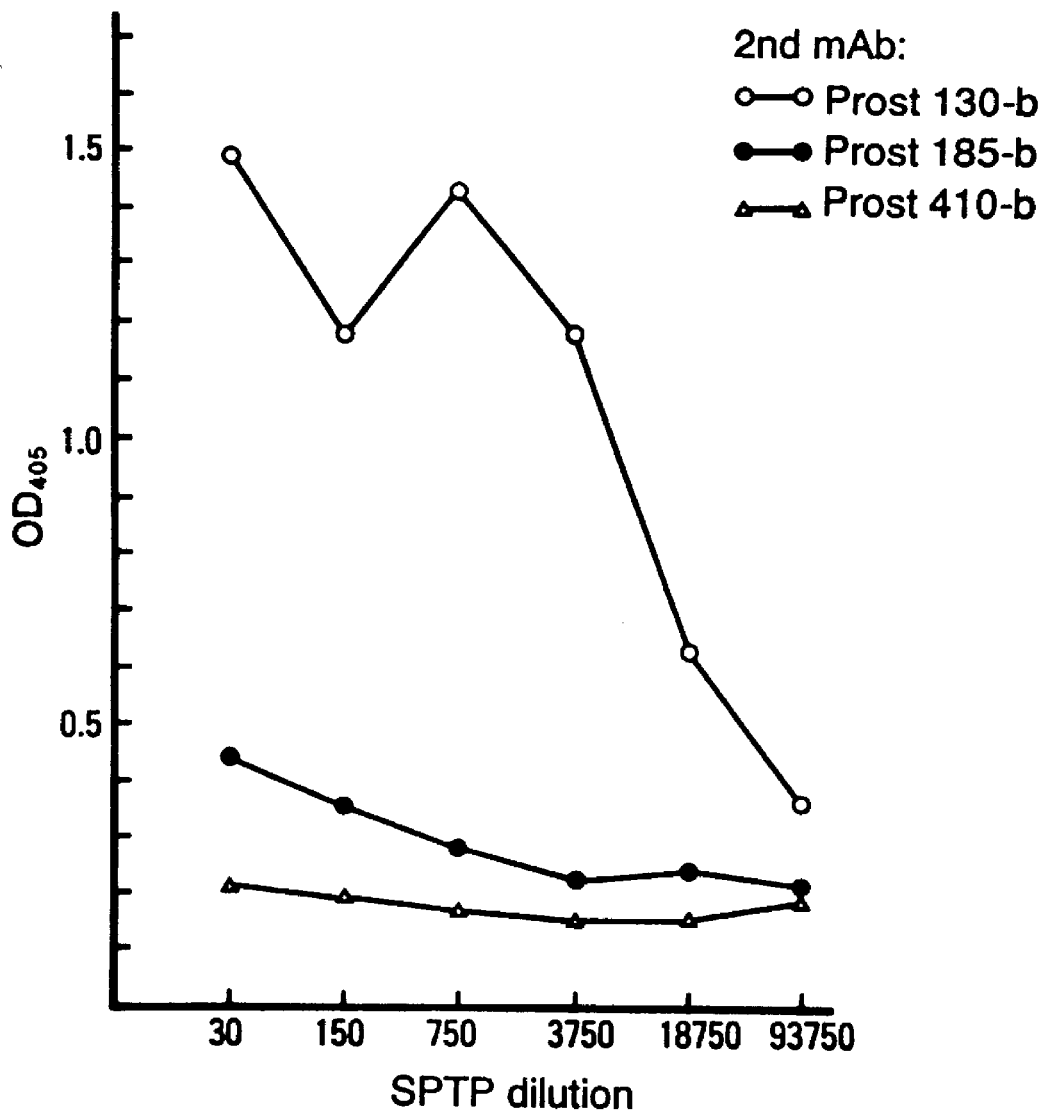

[a]Number of specimens with positive staining/number of specimens tested. Based on relative endpoint titrations with all 3 mAbs, immunoreactivity on prostate tissue was 200–500 fold that on other positive tissues.
n.t. = not tested mAb Prost 30 failed to react with paraffin sections. Immunofluorescence assay of fresh, viable prostate cells demonstrated cell surface fluorescence. The antigen recognized by Prost 30 was heat sensitive and resistant to treatment with 20 mM sodium periodate. Prost 30 did not react with either PSA or PAP by ELISA.

mAbs Prost 130 and Prost 185: As previously noted, mAbs Prost 130 and Prost 185 had virtually identical reactivity versus cell line targets (i.e., non-reactive; see Table 3) and tissue sections (Tables 5 and 6; see FIG. 2). While qualitatively not as tissue-specific as Prost 30, Prost 130 and 185 were quantitatively quite specific. That is, the IHC endpoint titers of Prost 130 and 185 were 200–500 fold higher on prostate tissue than on other IHC-reactive tissues. Like Prost 30, mAbs Prost 130 and 185 also failed to react with paraffin sections. Immunofluorescence assay of fresh, viable prostate cells demonstrated cell surface fluorescence. Both mAbs were reactive against SPTP by direct ELISA. Using a double antibody sandwich ELISA, antigen captured by Prost 130 was reactive with either Prost 130-biotin or Prost 185-biotin, but not with Prost 410-biotin, as a second antibody (FIG. 3A). Conversely, antigen captured using Prost 185 as a first antibody was reactive with Prost 130-biotin but non-reactive with either Prost 185-biotin or Prost 410-biotin as a second antibody (FIG. 3B). These results suggest that Prost 130 and Prost 185 recognize the same molecule, that this molecule has at least two Prost 130-reactive epitopes but only a single Prost 185-reactive epitope, and the antigen is not PSA.

Figure 4A:
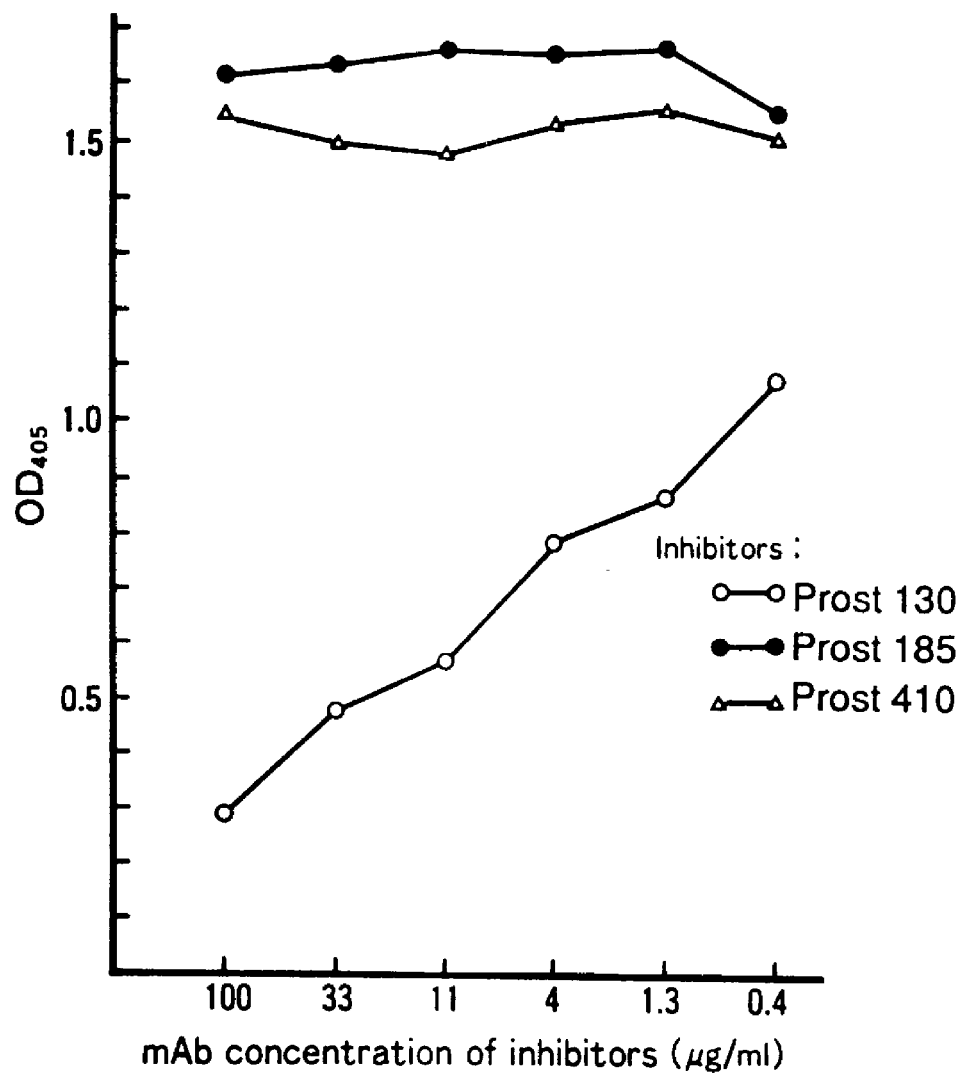
FIGS. 4A and 4B show an inhibition assay.
Figure 4B:
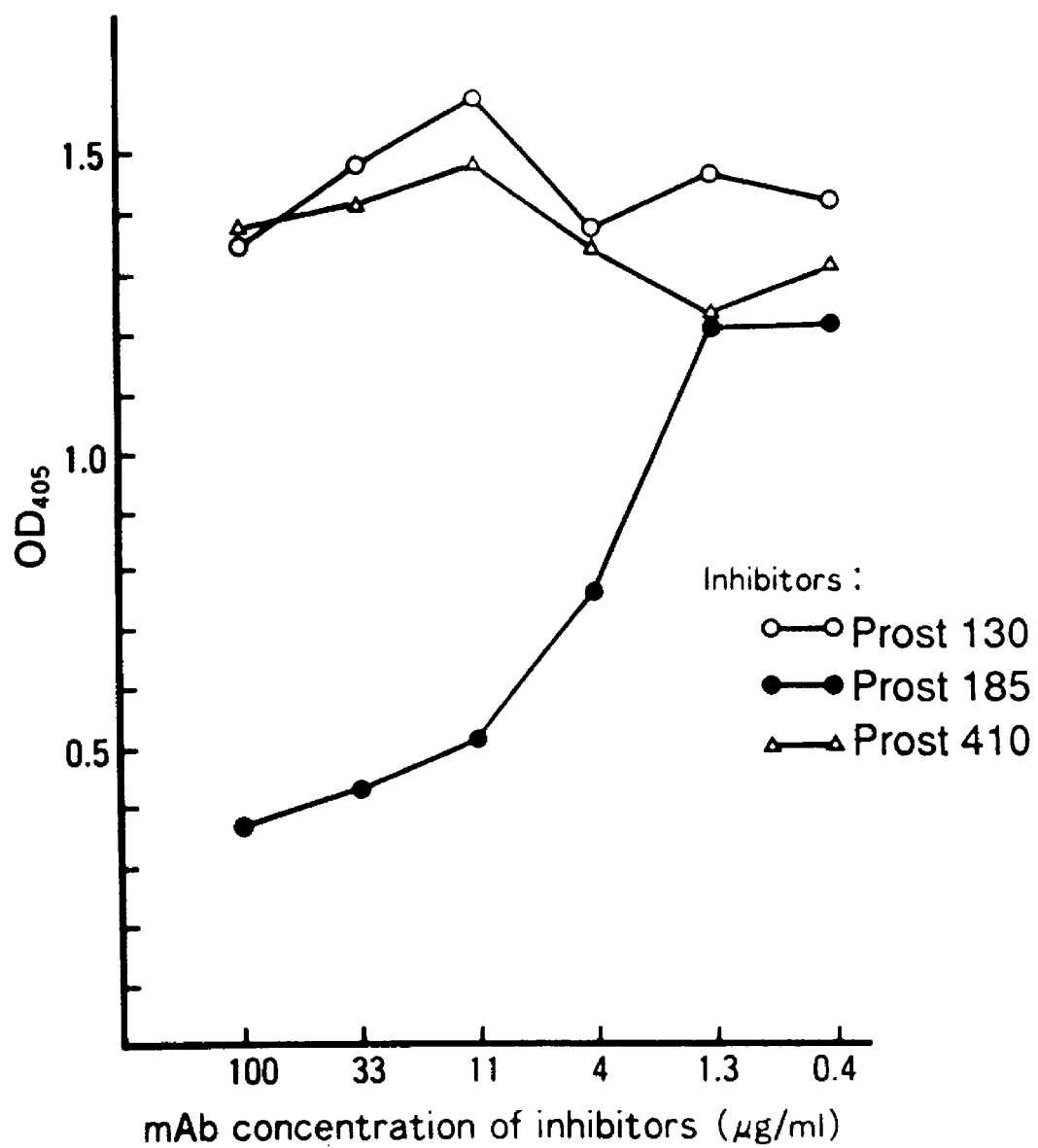

To confirm the Prost 130 and Prost 185 epitopes were different, a double antibody sandwich competitive ELISA was performed (Fig.. 4). Antigen from SPTP was captured by Prost 130. Unconjugated mAbs Prost 130, Prost 185, and Prost 410 were added to compete for binding by Prost 130-biotin (FIG. 4A). Only Prost 130, but neither Prost 185 or Prost 410, could inhibit Prost 130-biotin binding. Similarly, only Prost 185, but neither Prost 130 nor Prost 410, could inhibit Prost 185-biotin (FIG. 4B).

mAb Prost 410: Using the rabbit anti-mouse Ig MHA and an ELISA assay, purified Prost 410 at 40 $\mu$g/ml was reactive only with the LNCaP line of 83 human cell lines tested. By immunohistochemistry, it reacted with all normal, hyperplastic and neoplastic prostatic tissue sections tested (FIG. 1, Table 5). A sandwich ELISA assay demonstrated reactivity of Prost 410 to prostate specific antigen ("PSA"). The PSA reactivity of Prost 410 was confirmed by immunoprecipitation.

Previous efforts to develop mAbs to prostate-related molecules have been directed either toward previously characterized molecules of prostatic origin such as PAP or PSA or toward defining antigens which distinguish prostate cancer from normal or hyperplastic prostatic epithelium (i.e., BPH). In this study, a different approach was taken. A need for improved imaging of regional nodes was identified as a clinically valuable goal as this area represented such a common site of metastatic spread and yet one which has proven difficult to assess without a surgical staging procedure. The objective was to develop mAbs for use in clinical imaging of prostate cancer within the regional (pelvic) lymph nodes. A number of assumptions were made. First, the mAb need not specifically distinguish prostate cancer from BPH or normal prostate, because the presence of prostate antigen-expressing cells within a lymph node is, by definition, metastatic prostate cancer. It was felt that this broadening of the specificity requirement would substantially increase our likelihood of success. Secondly, administration of the mAb to patients via a selective, rather than a systemic, route (e.g., intra or periprostatic injection or via subcutaneous injection of the lower extremity was also anticipated). Both animal (Weinstein, J. N., et al., "Monoclonal Antibodies In The Lymphatics: Toward The Diagnosis And Therapy Of Tumor Metastases," Science, 218:1334–1337 (1982); Weinstein, J. N., et al., "Monoclonal Antibodies In The Lymphatics: Selective Delivery To Lymph Node Metastases Of A Solid Tumor," *Science,* 222:423–426 (1983); Parker, R. J., et al., "Targeting Of Murine Radiolabeled Monoclonal Antibodies In The Lymphatics," *Cancer Res.,* 47:2073–2076 (1987), which are hereby incorporated by reference) and human (Keenan, A. M., et al., "Immunolymphoscintigraphy In Patients With Lymphoma After Subcutaneous Injection Of Indium-111-Labeled T101 Monoclonal Antibody," *J. Nucl. Med.,* 28:42–46 (1987); Keenan, A. M., et al., "Immunolymphoscintigraphy And The Dose-Dependence Of Indium 111-Labeled T101 Monoclonal Antibody In Patients With Cutaneous T-Cell Lymphoma," Cancer Res., 47:6093–6099 (1987), which are hereby incorporated by reference). Studies have shown significant potential advantage by juxtaposing such anatomic selectivity to the inherent antigenic specificity of the mAb. The anticipated regional administration, therefore, allowed further liberalization of the mAbs' specificity requirement. This setting made it reasonable to screen and select clones simply on the basis of prostate reactivity in the absence of nodal reactivity.

Among the mAbs produced in this study, Prost 30, 130, and 185 appear different from previously defined prostate-related mAbs. For instance, mAbs PD41 (Beckett, M. L., et al., "Monoclonal Antibody PD41 Recognizes An Antigen Restricted To Prostate Adenocarcinomas," *Cancer Res.,* 51:1326–1333 (1987), which is hereby incorporated by reference), P25.48 and P25.91 (Bazinet, M., et al., "Immunohistochemical Characterization Of Two Monoclonal Antibodies, P25.48 And P25.91, Which Define A New Prostate-Specific Antigen," *Cancer Res.,* 48:6938–6942 (1988), which is hereby incorporated by reference), and P6.2 (Wright, G. L., Jr., et al., "Immunohistochemical Localization Of Prostate Carcinoma-Associated Antigens," *Cancer Res.,* 43:5509–5516 (1983), which is hereby incorporated by reference) define antigens restricted to a subset of prostate cancers but not expressed by either normal or hyperplastic prostatic epithelial cells. Among the mAbs which define antigens shared by normal, hyperplastic, and neoplastic prostatic cells, clone 35 (Frankel, A. E., et al., "Monoclonal Antibodies To Human Prostate Antigen," *Cancer Res.,* 42:3714–3718 (1982), which is hereby incorporated by reference), differs from those mAbs reported here by virtue of clone 35's reactivity with breast epithelium and bladder cancer cell line T-24. When clone 35 is assayed by a membrane radioimmunoassay ("RIA"), it is more reactive with normal kidney than prostate tissue. Clone 24 (Frankel, A. E., et al., "Monoclonal Antibodies To Human Prostate Antigen," Cancer Res., 42:3714–3718 (1982), which is hereby incorporated by reference), is reactive with the PC-3 cell line and, in a membrane RIA, demonstrated high reactivity to BPH but only background reactivity with prostate cancer. mAb αPro3 (Ware, J. L., et al., "Production Of Monoclonal Antibody αPro3 Recognizing A Human Prostatic Carcinoma Antigen," *Cancer Res.,* 42:1215–1222 (1982), which is hereby incorporated by reference), bound PC-3 cells, and, although Immunohistochemistry was not performed, an absorption assay utilizing tissue extracts appears to indicate greater antigen expression in a wide range of non-prostatic tissues than in BPH. The epitopes detected by mAbs F77 (Carroll, A. M., et al., "Monoclonal Antibodies To Tissue-Specific Cell Surface Antigens," *Clin. Immunol. And Immunopathol.,* 33:268–281 (1984), which is hereby incorporated by reference), KR-P8 (Raynor, R. H., et al., "Characterization of a Monoclonal Antibody, KR-P8, That Detects A New Prostate-Specific Marker," *J. Natl. Cancer Inst.,* 73:617–625 (1984); Raynor, R. H., et al., "Biochemical Nature Of The Prostate-Associated Antigen Identified By The Monoclonal Antibody," KR-P8, Prostate, 9:21–31 (1986), which are hereby incorporated by reference), TURP-27 and TURP-73 (Starling, J. J., et al., "Human Prostate Tissue Antigens Defined By Murine Monoclonal Antibodies," *Cancer Res.,* 46:367–374 (1986), which is hereby incorporated by reference) are detectable on formalin fixed/paraffin embedded tissue sections unlike either Prost 30, 130, or 185. The TURP-73 antigen is also detectable on several prostate cancer cell lines. One previously reported mAb, 7E11-C5 (Horoszewicz, J. S., et al., "Monoclonal Antibodies To A New Antigenic Marker In Epithelial Prostatic Cells And Serum Of Prostatic Cancer Patients," *Anticancer Res.,* 7:927–936, (1987), which is hereby incorporated by reference), has some characteristics similar to Prost 30, 130, and 185. These similarities include lack of reactivity with cell lines, weak immunohistochemical reactivity with some renal tubules, and reactivity with all normal, BPH, and neoplastic prostates tested. There are, however, features which differ: 7Ell-C5 reacts with LNCap cells after fixation, it has immunohistochemical reactivity with skeletal muscle (Lopes, A. D., et al., "Immunohistochemical And Pharmacokinetic Characterization Of The Site-Specific Immunoconjugate CYT-356 Derived From Antiprostate Monoclonal Antibody 7E11-C5, " *Cancer Res.,* 50:6423–6429, (1990), which is hereby incorporated by reference) and, at least in the initial report, the presence of the 7E11-C5 Ag in serum (Horoszewic, J. S., et al., "Monoclonal Antibodies To A New Antigenic Marker In Epithelial Prostatic Cells And Serum Of Prostatic Cancer Patients," *Anticancer Res.,* 7:927–936, (1987), which is hereby incorporated by reference.

Among the previously published mAbs, some have already begun clinical evaluation for imaging prostate cancer (Vihko, P., et al., "Radioimaging Of Prostatic Carcinoma With Prostatic Acid Phosphatase—Specific Antibodies," *Biotechnology In Diagnostics,* pp. 131–134 (1985); Babaian, R. J., et al., "Radioimmunological Imaging Of Metastatic Prostatic Cancer With 111-Indium-Labeled Monoclonal Antibody PAY 276", *J. Urol.,* 137:439–443 (1987); Leroy, M., et al., "Radioimmunodetection Of Lymph Node Invasion In Prostatic Cancer. The Use Of Iodine 123 (123-I) -Labeled Monoclonal AntiProstatic Acid Phosphatase (PAP) 227 A F(ab')2 antibody Fragments In Vivo," *Cancer,* 64:1–5 (1989); Meyers, J. F., et al., "Development Of Monoclonal Antibody Imaging Of Metastatic Prostatic Carcinoma," *The Prostate,* 14:209–220 (1989), which are hereby incorporated by reference). For example, mAbs to PSA have been used for imaging without apparent success (Meyers, J. F., et al., "Development Of Monoclonal Antibody Imaging Of Metastatic Prostatic Carcinoma," *The Prostate,* 14:209–220, (1989), which is hereby incorporated by reference). Given the nature of the PSA antigen, this is probably not surprising. While PSA is very tissue-specific, the antigen is primarily cytoplasmic with little, if any, cell surface expression (Warhol, J. J., et al., "The Ultrastructural Localization Of Prostatic Specific Antigen And Prostatic Acid Phosphatase In Hyperplastic And Neoplastic Human Prostates," *J. Urol.,* 134:607–613 (1985), which is hereby incorporated by reference). Furthermore, PSA is secreted and can be detected in serum. Systemic administration of antibody to PSA would be expected to result in immune complex formation, uptake in the reticuloendothelial system and consequent background imaging.

mAbs to PAP have also been studied for imaging (Vihko, P., et al., "Radioimaging Of Prostatic Carcinoma With Prostatic Acid Phosphatase—Specific Antibodies," *Biotech-*

*nology In Diagnostics*, pp. 131–134, (1985); Leroy, M., et al., "Radioimmunodetection Of Lymph Node Invasion In Prostatic Cancer. The Use Of Iodine 123 (123-I)-Labeled Monoclonal Anti-Prostatic Acid Phosphatase (PAP) 227 A F(ab')2 Antibody Fragments In Vivo," *Cancer*, 64:1–5, (1989), which are hereby incorporated by reference). While PAP has features similar to PSA such as being primarily a cytoplasmic, secreted antigen, trials using a regional, i.e., periprostatic injection have claimed initial success (Leroy, M., et al., "Radioimmunodetection Of Lymph Node Invasion In Prostatic Cancer. The Use Of Iodine 123 (123-I) -Labeled Monoclonal Anti-Prostatic Acid Phosphatase (PAP) 227 A F(ab')2 Antibody Fragments In Vivo," *Cancer*, 64:1–5 (1989), which is hereby incorporated by reference). Perhaps, the shortcomings of such an antigenic target may be overcome by selective/regional administration.

The antibodies Prost 130 and Prost 185 appear worthy of study via such a selective site administration. These antibodies target at least 3 epitopes on the detected antigen, the antigen is strongly expressed at the cell surface and it does not circulate. The normal tissues which express Prost 130/ Prost 185 (thymus, parotid, colon, foreskin, and placenta) should not present a significant practical problem.

Another mAb currently being evaluated for use in imaging, as well as therapy, is CYT-356 (Lopes, A. D., et al., "Immunohistochemical And Pharmacokinetic Characterization Of The Site-Specific Immunoconjugate CYT-356 Derived From Antiprostate Monoclonal Antibody 7E11-C5," *Cancer Res.*, 50:6423–6429 (1990); Wynant, G. E., "Immunoscintigraphy Of Prostatic Cancer: Preliminary Results With $^{111}$In-Labeled Monoclonal Antibody 7E11-C5.3 (CYT-356), *The Prostate*, 18:229–241" (1991), which are hereby incorporated by reference), a subclone of 7E11-C5 (Horoszewicz, J. S., et al., "Monoclonal Antibodies To A New Antigenic Marker In Epithelial Prostatic Cells And Serum Of Prostatic Cancer Patients," *Anticancer Res.*, 7:927–936 (1987); Lopes, A. D., "Immunohistochemical And Pharmacokinetic Characterization Of The Site-Specific Immunocojugate CYT-356 Derived From Antiprostate Monoclonal Antibody 7E11-C5," *Cancer Res.*, 50:6423–6429 (1990), which are hereby incorporated by reference). As noted, there are some similarities between this mAb and Prost 30. Initial imaging results with CYT-356 appear promising (Wynant, G. E., et al., "Immunoscintigraphy Of Prostatic Cancer: Preliminary Results With $^{111}$In-Labeled Monoclonal Antibody 7E11-C5.3 (CYT-356)," *The Prostate*, 18:229–241 (1991), which is hereby incorporated by reference).

mAb Prost 30 appears to have some optimal characteristics for localization to normal and neoplastic prostate either by regional or systemic administration. Indeed, mAb Prost 30 shares many features with another antibody—mAb G250—which has already been demonstrated to be successful in clinical trials of patients with renal cancer. See Oosterwijk, E., et al., "Antibody Localization In Human Renal Cell Carcinoma: A Phase I Study Of Monoclonal Antibody G250," *J. Of Clin. Oncol.*, 11:738–750 (1993), which is hereby incorporated by reference). These common features include isotype ($\gamma_1$), a high degree of specificity by immunohistochemistry, cell surface expression and absence of circulating antigen. With G250, specific, high level accumulation in both primary and metastatic renal cancer sites in the absence of normal tissue uptake has been demonstrated. The immunoscintigraphy study demonstrated high sensitivity (3 of 12 patients had sites of disease detected on mAb G250 scans which were not diagnosed by conventional studies) and high (100%) specificity—all mAb detected sites have been histopathologically confirmed renal cancers. The potential for mAb localization to metastatic prostate cancer sites may provide utility not only in diagnostic immunoscintigraphy but also for antibody directed therapy of metastatic disease. Potential localization to normal or hyperplastic prostate should not represent a significant problem. Indeed, this might be viewed as an advantage. If it can be shown that Prost 30 localizes well to the prostate, the antibody could have clinical potential for treatment of localized carcinoma of the prostate (alone or in combination with other therapies), in the treatment of BPH, or even in the prevention of BPH or prostate cancer.

Example 10

Clinical Data

Fifteen patients with a diagnosis of prostate cancer have received $^{131}$Iodine (10 mCi)-labeled mab Prost 30 intravenously 1 week prior to either surgery (i.e., radical prostatectomy) or biopsy of a suspicious lesion. In the week between Prost 30 injection and surgery/biopsy, patients underwent whole body radionuclide scanning on 2–3 occasions and one SPECT scan. Successive patients, in cohorts of 3, received escalating doses of Prost 30 (all with 10 mCi $^{131}$Iodine): 1.0 mg (3 patients), 2.0 mg (3 patients), 5.0 mg (3 patients), 10.0 mg (3 patients), and 20.0 mg (3 patients).

Figure 5:
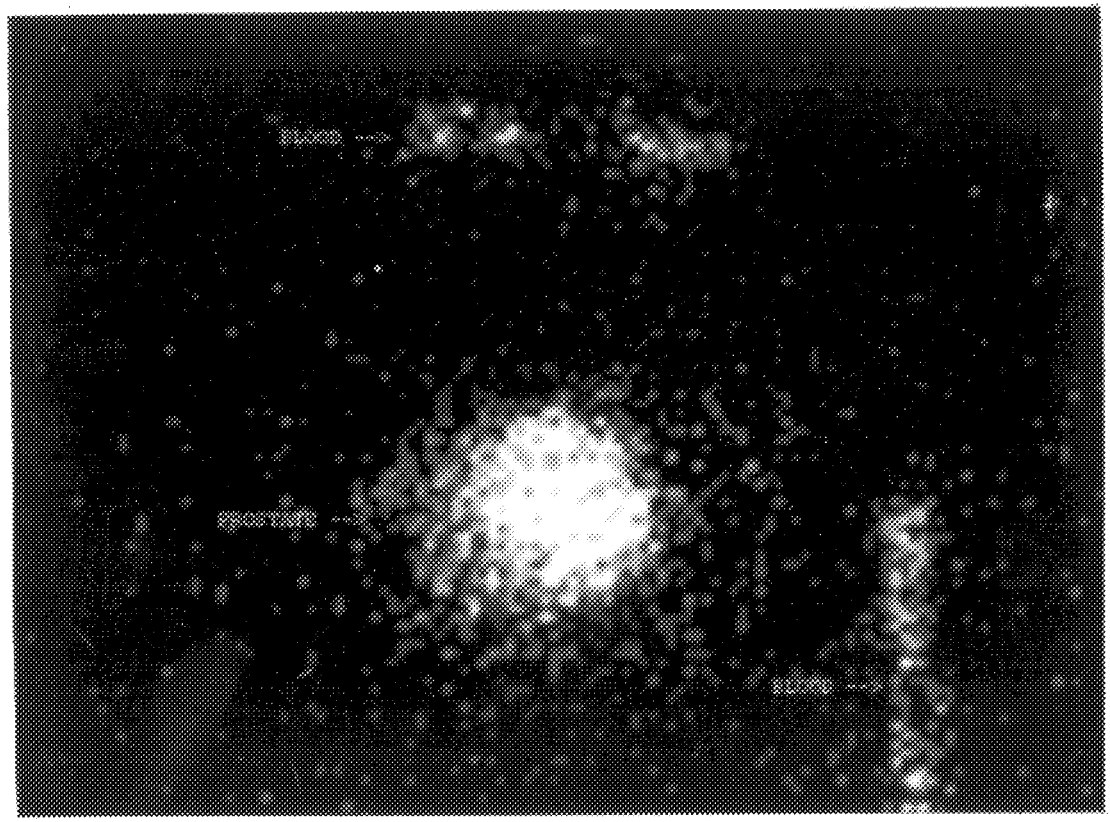
FIG. 5 shows a resected prostate with two adjacent tubes of blood at right angles to each other. The latter was drawn at the same time as the prostate was resected—i.e., one week after 131I-Prost 30 administration. The color intensity is directly proportional to the radioactivity. This figure shows that the radiolabeled antibody 1) localizes to the prostate and 2) actually concentrates in the prostate at far higher levels than the blood and remains in the prostate for >one week.

Of the 15 patients, 14 had a prostate gland in situ. In all of these cases, the prostate gland could be visualized on the whole-body and spect images. The 1 patient without a prostate in situ showed no Prost 30 localization to the prostatic bed, demonstrating specificity and absence of false-positives. Two patients had demonstrable metastatic disease by conventional CT scans. In both cases, the monoclonal antibody images visualized these sites (one patient: lymph nodes plus liver; second patient: lymph nodes). In 3 cases, the resected prostate specimen was scanned/imaged alongside tubes of blood drawn at the time of resection. These images (see FIG. 5) demonstrate substantial specific and selective accumulation and concentration of the labeled Prost 30 in the prostate (target site of disease) relative to the blood or other normal tissues. This indicates that wherever prostate cells may be in the body (e.g., lymph node, bone marrow, etc.), Prost 30 will bind to those cells.

Two patients entered in the above study had progressive hormone-refractory disease with rising prostate specific antigens ("PSA") prior to entry. Subsequent to Prost 30 administration, their PSAs reversed course and dropped substantially (by approx 75%). The PSAs did not return to pre-treatment baseline levels for 9–10 months. Three patients who were not previously treated with hormonal therapy were given hormonal therapy shortly after Prost 30. Their PSAs have fallen to and remained at undetectable levels. Five patients, including 4 at high risk of relapse (i.e., with high pre-treatment PSA and adverse pathological features) had Prost 30 plus surgery. None of these patients have yet relapsed. One patient received Prost 30 followed by radiation therapy. Although at high risk of failure given his pre-treatment PSA, imaging studies and biopsy results, he too remains a complete responder with undetectable serum PSA levels and no evidence of disease. The above results indicate that the Prost 30 antibody itself has a therapeutic effect. Only 1 mg of the administered dose was actually labeled with $^{131}$I, while the balance of the administered dose (0 to 19 mg) did not contain iodine. The $^{131}$Iodine label attached to the Prost 30 monoclonal antibody is simply a tracer dose in a quantity insufficient to explain the therapeutic effect.

Two of seven patients did not develop any evidence of human anti-mouse antibody (HAMA) formation, as defined by a very sensitive assay, after Prost 30 treatment. The 2 hormone-refractory patients did not develop HAMA.

A phase I/II therapy trial with unconjugated Prost 30 has begun. The first 2 patients entered are also showing PSA declines, indicating therapeutic benefit.

Example 11

C37 and C219 Monoclonal Antibodies

BALB/c mice were immunized once with a cell suspension of the LNCaP human prostate cancer cell line. Approximately four days later, the mice were sacrificed and spleens harvested for preparation of hybridomas. This immunization design is optimized for production of IgM antibodies which are the strongest at complement fixation (i.e., they are the best at mediating complement lysis of target cells). IgMs are often avoided in monoclonal work because they are very large molecules (5–10×larger than IgGs), and there are concerns about them being able to penetrate into tumor deposits. This could be an advantage, because the predominant site of metastatic disease is bone marrow and lymph nodes which should be readily accessible to IgMs. Conversely, normal tissues will be exposed to lower levels of these IgMs decreasing the chances of cross-reaction.

Candidate antibodies were screened and selected using a complement fixation assay with the immunizing cell line (LNCaP) as a target. That is, the hybridoma supernatants were incubated with the target cells in the presence of human serum (i.e. the source of complement) and the hybridomas whose supernatants lysed/killed the target cells were selected. Any antibodies which also lysed non-prostate cells were not selected. As a result, two clones, designated C37 and C219, which are very potent and specific at lysing LNCaP, were identified. Furthermore, when they were combined, these antibodies did not function in an additive manner, but in a synergistic one.

An approach that uses cytotoxic mechanisms, such as complement, has inherent advantages over methods which use conjugated agents. It avoids the necessity of linking an agent to the antibody, such conjugation is a developing science unto itself. It also eliminates all of the issues related to how those agents kill the cells. For example, the concept of using radioisotopes not only is complicated due to the linkage issues, but so is the science of radio emitters. Does one use alpha, beta, or gamma emitters? Does one need internalized or non-internalized antigens? Using these endogenous cytotoxic mechanisms such as complement-mediated cytoxicity also eliminates the side effects of conjugated agents. It also makes handling and preparation of the therapeutic dramatically simpler. Furthermore, the complement system is itself a self-amplifying one. That is, as each successive enzyme in the cascade is activated, it, in turn, activates many more molecules and becomes an amplified process.

Part of the effect of triggering the complement system is that it also recruits leukocytes, including immune cells, into the area by release of chemotactic factors. As a result, the complement system generates quite a substantial and amplified immune response, both cellular and humoral, with the use of antibody alone as the triggering mechanism.

Although the invention has been described in detail for the purpose of illustration, it is understood that such detail is solely for that purpose and variations can be made by those skilled in the art without departing from the spirit and scope of the invention which is defined by the following claims.

What is claimed:

1. An isolated antibody or binding portion thereof recognizing an antigen of normal, benign, hyperplastic, and cancerous prostate epithelial cells or portions thereof but no antigens circulating in blood, said antibody or binding portion thereof being immunoreactive with the prostate epithelial cells at a level 200–500 fold greater than for other tissue, based on immunohistochemical endpoint titrations, wherein said antibody or binding portion thereof binds to the same epitope of the prostate-related antigen as those to which monoclonal antibodies produced from hybridoma cell lines having ATCC Designations HB 11424, HB 11425, HB 11426, HB 11427, HB 11892, or HB 11893 bind.

2. An isolated antibody or binding portion thereof according to claim 1, wherein the isolated antibody or binding portion thereof is an antibody selected from the group consisting of a monoclonal antibody and a polyclonal antibody.

3. An isolated antibody or binding portion thereof according to claim 2, wherein the antibody is a monoclonal antibody produced from a hybridoma cell line selected from the group consisting of the hybridoma cell lines having ATCC Designations HB 11424, HB 11425, HB 11426, HB 11427, HB 11892, and HB 11893.

4. An isolated antibody or binding portion thereof according to claim 2, wherein the isolated antibody or binding portion thereof is a binding portion of an antibody selected from the group consisting of a Fab fragment, a F(ab')$_2$ fragment, and a Fv fragment.

5. An isolated antibody or binding portion thereof according to claim 1, wherein the antibody or binding portion thereof is bound to a cytotoxic drug.

6. An isolated antibody or binding portion thereof according to claim 5, wherein the cytotoxic drug is selected from the group consisting of a therapeutic drug, a compound emitting radiation, molecules of plant, fungal, or bacterial origin, biological proteins, and mixtures thereof.

7. A composition comprising:
   an antibody or binding portion thereof according to claim 5 and
   a physiological acceptable carrier, excipient, or stabilizer mixed with the antibody or binding portion thereof.

8. A composition comprising:
   an antibody or binding portion thereof according to claim 5 and
   a pharmaceutically acceptable carrier, excipient, or stabilizer mixed with the antibody or binding portion thereof.

9. An isolated antibody or binding portion thereof according to claim 1, wherein said antibody or binding portion thereof is bound to a detectable label.

10. An isolated antibody or binding portion thereof according to claim 9, wherein the label is selected from the group consisting of a fluorescent label, a biologically-active enzyme label, a radioactive label, a nuclear magnetic resonance active label, a luminescent label, and a chromophore label.

11. A composition comprising:
    an antibody or binding portion thereof according to claim 9 and
    a physiological acceptable carrier, excipient, or stabilizer mixed with the antibody or binding portion thereof.

12. A composition comprising:
    an antibody or binding portion thereof according to claim 9 and
    a pharmaceutically acceptable carrier, excipient, or stabilizer mixed with the antibody or binding portion thereof.

13. A kit for detecting prostate cancer comprising:

an antibody or binding portion thereof according to claim 9 and means to detect the label.

14. A kit according to claim 13, wherein the label is selected from the group consisting of a fluorescent label, a biologically-active enzyme label, a radioactive label, a nuclear magnetic resonance active label, a luminescent label, and a chromophore label.

15. A kit according to claim 13, wherein said antibody or binding portion thereof is a monoclonal antibody produced from a hybridoma cell line selected from the group consisting of the hybridoma cell lines having ATCC Designations HB 11424, HB 11425, HB 11426, HB 11427, HB 11892, and HB 11893.

16. A kit according to claim 13, wherein the antibody or binding portion thereof is in a composition further comprising a physiological acceptable carrier, excipient, or stabilizer.

17. A kit according to claim 13, wherein the antibody or binding portion thereof is in a composition further comprising a pharmaceutically acceptable carrier, excipient, or stabilizer.

18. A hybridoma cell line that produces a monoclonal antibody recognizing an antigen of normal, benign, hyperplastic, and cancerous prostate epithelial cells or portions thereof but no antigens circulating in blood, wherein said monoclonal antibody binds to the same epitope of the prostate-related antigen as those to which monoclonal antibodies produced from hybridoma cell lines having ATCC Designations HB 11424, HB 11425, HB 11426, HB 11427, HB 11892, or HB 11893 bind.

19. An isolated antibody or binding portion thereof according to claim 1 which recognizes an antigen found in all normal, benign, hyperplastic, and cancerous prostate epithelial cells or portions thereof.

* * * * *

UNITED STATES PATENT AND TRADEMARK OFFICE
CERTIFICATE OF CORRECTION

PATENT NO. : 5,773,292

DATED : June 30, 1998

INVENTOR(S) : Neil H. Bander

It is certified that error appears in the above-identified patent and that said Letters Patent is hereby corrected as shown below:

Title page, item [73] Assignee, "Cornell University" should be replaced with --Cornell Research Foundation, Inc.--

Signed and Sealed this

Nineteenth Day of January, 1999

Attest:

Attesting Officer

*Acting Commissioner of Patents and Trademarks*